(12) United States Patent
Ng et al.

(10) Patent No.: US 8,779,207 B2
(45) Date of Patent: Jul. 15, 2014

(54) METHOD FOR SYNTHESIS OF [6,6]-PHENYL-C61-BUTYRIC ACID METHYL ESTER (PCBM) AND FULLERENE DERIVATIVES

(75) Inventors: Ka Ming Ng, Hong Kong (CN); Jianle Zhuang, Hong Kong (CN); Nai Wen Tseng, Hong Kong (CN); Yong Yu, Hong Kong (CN)

(73) Assignee: Nano and Advanced Materials Institute Limited, Clear Water Bay, Kowloon (HK)

( * ) Notice: Subject to any disclaimer, the term of this patent is extended or adjusted under 35 U.S.C. 154(b) by 18 days.

(21) Appl. No.: 13/601,371

(22) Filed: Aug. 31, 2012

(65) Prior Publication Data
US 2014/0066647 A1 Mar. 6, 2014

(51) Int. Cl.
*C07C 45/00* (2006.01)

(52) U.S. Cl.
USPC .......................................... 568/308; 568/319

(58) Field of Classification Search
USPC .................................. 568/308, 319
See application file for complete search history.

(56) References Cited

U.S. PATENT DOCUMENTS

2011/0130588 A1* 6/2011 Uetani et al. .................. 560/103
2012/0123058 A1* 5/2012 Ohno et al. .................... 525/284

OTHER PUBLICATIONS

Hummelen et al. Preparation and Characterization of Fulleroid and Methanofullerene Derivatives. Journal of Organic Chemistry, 1995, vol. 60, pp. 532-538.*
Gonzalez et al. The Specifi Acid-Catalyzed and Photochemical Isomerization of a Robust Fulleroid to a Methanofullerene. Journal of Organic Chemistry, 1995, vol. 60, pp. 2618-2620.*
Zheng et al. Methanofullerenes Used as Electron Acceptors in Polymer Photovoltaic Devices. Journal of Physical Chemistry B, 2004, vol. 108, pp. 11921-11926.*

* cited by examiner

*Primary Examiner* — Sikarl Witherspoon
(74) *Attorney, Agent, or Firm* — Nath, Goldberg & Meyer; Joshua B. Goldberg; Scott H. Blackman

(57) ABSTRACT

The present subject matter relates to methods for the synthesis of [6,6]-phenyl-$C_{61}$-butyric acid methyl ester (PCBM) and fullerene derivatives in a yield of at least 40%.

13 Claims, 4 Drawing Sheets

METHOD FOR SYNTHESIS OF [6,6]-PHENYL-C61-BUTYRIC ACID METHYL ESTER (PCBM) AND FULLERENE DERIVATIVES

TECHNICAL FIELD

The present subject matter relates to a method for the synthesis of [6,6]-phenyl-C$_{61}$-butyric acid methyl ester (PCBM) and fullerene derivatives.

BACKGROUND

Significant progress has been made in the development of thin-film organic electronic devices such as photovoltaic cells, transistors, photodetectors, sensors, and other devices for commercial application. Many of these devices utilize solution-processable semiconductors based on fullerene derivatives in pure form. The most commonly used fullerene derivative is phenyl-C$_{61}$-butyric-acid-methyl-ester (PCBM), which is classified as a methanofullerene.

PCBM is an analogue of [60]PCBM from C$_{60}$ fullerene. [70]PCBM has been used as a semiconductor in organic electronics, particularly for polymer solar devices (WIENK et al., Angewadte Chemie, 2003, (115), 3493-3497) and transistors (Anthopoulos et al., Journal of Applied Physics, (98), 054503).

Previous methods for obtaining PCBM have resulted in a yield of 35% at most (Hummelen et al., J. Org. Chem 1995, 60, 532). In the production method of Yang et al., Carbon 2007, 45, 2951, the yield of PCBM was only 33.6% at most.

A higher yield of PCBM is greatly desired due to its widespread use as a solution-processable semiconductor for thin-film organic electronic devices.

SUMMARY

The present subject matter relates to a method for the synthesis of a compound having Formula I or a stereoisomer thereof. In one embodiment, this synthetic method comprises a reaction between a fullerene and a compound having Formula II:

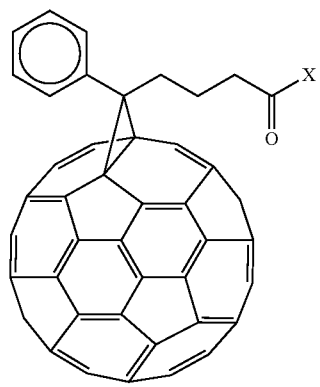

FORMULA I

FORMULA II wherein X is C$_n$H$_{2n+1}$, R is C$_n$H$_{2n+1}$, and n=0 to 20; wherein the fullerene is selected from the group consisting of C$_{60}$, C$_{70}$, C$_{76}$, C$_{78}$, C$_{84}$, and C$_{90}$; wherein the fullerene and the compound having Formula II are present in the reaction at a molar ratio ranging from 1:2 to 2:1; and wherein the reaction produces at least a 40% yield of the compound having Formula I.

In one embodiment, the compound having Formula I is [6,6]-phenyl-C$_{61}$-butyric acid methyl ester (PCBM) or [5,6]-phenyl-C$_{61}$-butyric acid methyl ester (F1-OMe). The chemical structures of each are shown below.

F1-OMe

PCBM

In another embodiment, the present subject matter relates to a method for the synthesis of a compound having Formula I or a stereoisomer thereof comprising a first reaction and a second reaction; the first reaction comprising mixing a basic reagent with a compound having Formula II to produce a diazoalkane; the second reaction comprising mixing the diazoalkane produced from the first reaction with a fullerene; wherein the fullerene is selected from the group consisting of $C_{60}$, $C_{70}$, $C_{76}$, $C_{78}$, $C_{84}$, and $C_{90}$; wherein the compound having Formula II and the basic reagent are present in the first reaction at a molar ratio ranging from 1:2 to 2:1; and wherein the first reaction and the second reaction produce at least a 40% yield of the compound having Formula I.

In another embodiment, PCBM is synthesized by heating F1-OMe within o-dichlorobenzene. The reaction scheme for this is shown as follows.

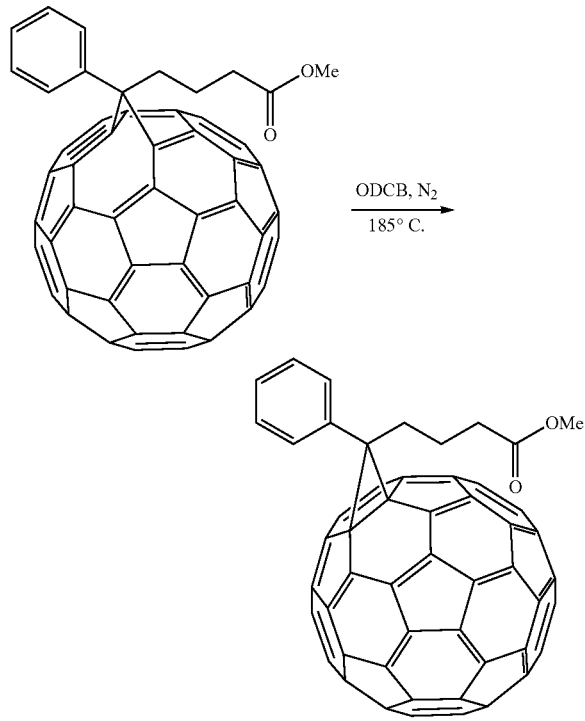

DETAILED DESCRIPTION

Definitions

Figure 1:
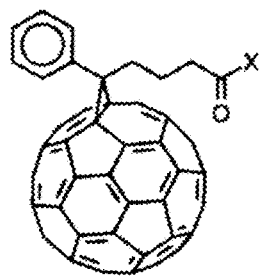
FIG. 1 shows the chemical structure of the compound having Formula I.
Figure 2:
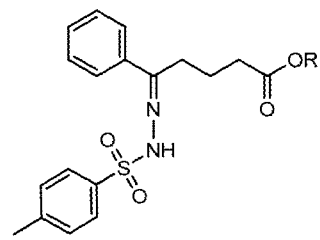
FIG. 2 shows the chemical structure of the compound having Formula II.
Figure 3:
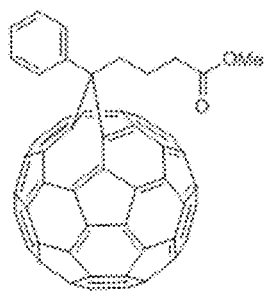
FIG. 3 shows the chemical structure of F1-OMe.
Figure 4:
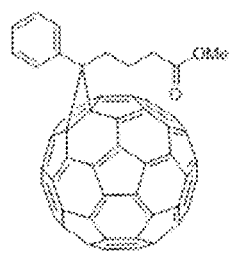
FIG. 4 shows the chemical structure of PCBM.
Figure 5:
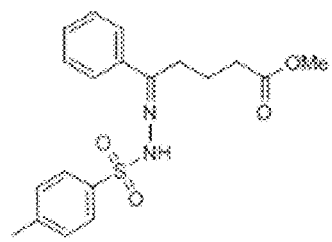
FIG. 5 shows the chemical structure of MBT.
Figure 6:
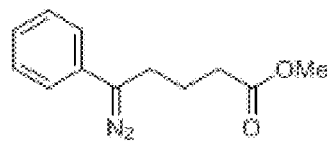
FIG. 6 shows the chemical structure of 1-phenyl-1-(3-(methoxycarbonyl)propyl)diazomethane.

All technical and scientific terms used herein have the same meanings as commonly understood by someone ordinarily skilled in the art to which this subject matter belongs. The following definitions are provided for the purpose of understanding the present subject matter and for constructing the appended patent claims.

As used herein, the term "diazoalkane" relates to any diazo compound having the general formula $R_2CN_2$, where R is hydrogen or any saturated organic group.

As used herein, the term "fullerene" relates to any molecule composed entirely of carbon, in the form of a hollow sphere, ellipsoid, or tube. In preferred embodiments, the fullerenes useful herein can contain 60, 70, 76, 78, 84, or 90 carbon atoms.

As used herein, the term "isomer" relates to different compounds that have the same molecular formula and includes cyclic isomers and other isomeric forms of cyclic moieties.

As used herein, the term "stereoisomer" relates to isomers that differ only in the way the atoms are arranged in space.

The term "a" or "an" as used herein includes the singular and the plural, unless specifically stated otherwise. Therefore, the term "a," "an" or "at least one" can be used interchangeably in this application.

Throughout the application, descriptions of various embodiments use the term "comprising"; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used herein, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Other terms as used herein are meant to be defined by their well-known meaning in the art.

The present subject matter relates to a method for the synthesis of a compound having Formula I or a stereoisomer thereof comprising a reaction between a fullerene and a compound having Formula II:

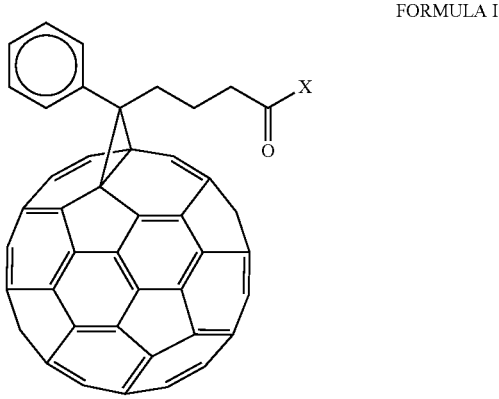

FORMULA I

-continued

FORMULA II

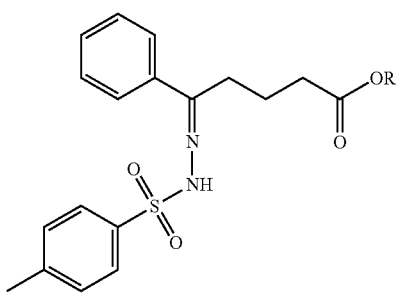

wherein X is $C_nH_{2n+1}$, R is $C_nH_{2n+1}$, and n=0 to 20; wherein the fullerene is selected from the group consisting of $C_{60}$, $C_{70}$, $C_{76}$, $C_{78}$, $C_{84}$, and $C_{90}$; wherein the fullerene and the compound having Formula II are present in the reaction at a molar ratio ranging from 1:2 to 2:1; and wherein the reaction produces at least a 40% yield of the compound having Formula I.

In one embodiment, the compound having Formula I is [6,6]-phenyl-$C_{61}$-butyric acid methyl ester (PCBM) or [5,6]-phenyl-$C_{61}$-butyric acid methyl ester (F1-OMe). The chemical structures of each are shown below.

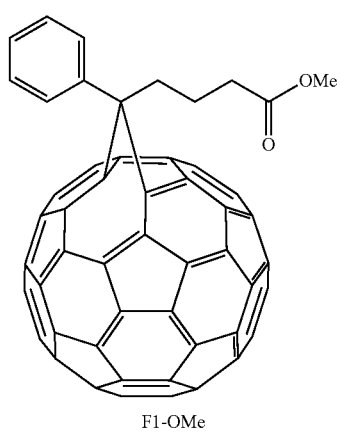

F1-OMe

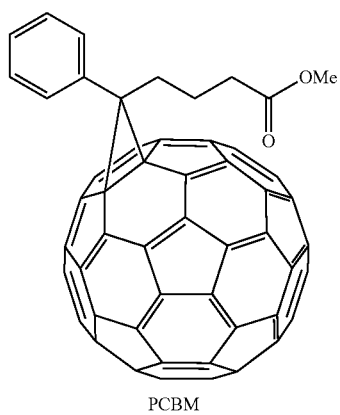

PCBM

In one such embodiment, the compound having Formula II is a tosylhydrazone such as methyl 4-benzoylbutyrate p-tosylhydrazone (MBT). The chemical structure of MBT is shown below.

In one embodiment, where the compound having Formula II is MBT and the fullerene is $C_{60}$, the reaction scheme is as follows.

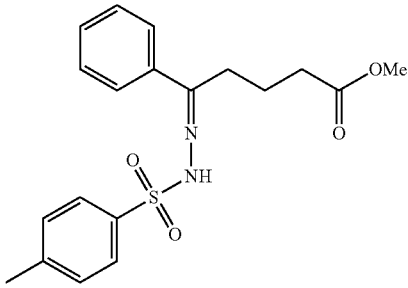 [SMILES: COC(=O)CCCC(=NNS(=O)(=O)c1ccc(C)cc1)c1ccccc1]

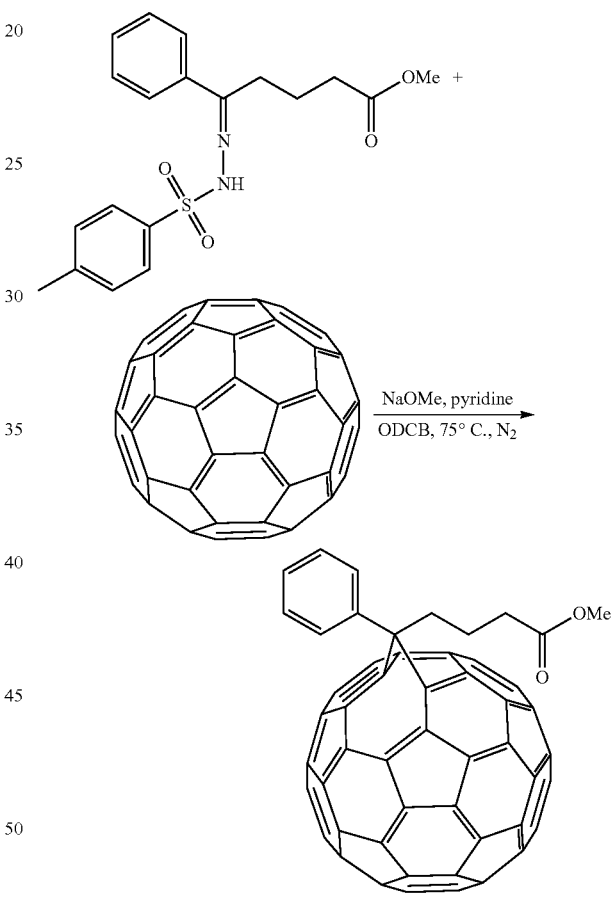

In one embodiment, the fullerene and the compound having Formula II are preferably present in the reaction at a molar ratio of 1:1.

In another aspect of the present subject matter, the reaction also produces no more than a 22% yield of a byproduct.

In still another embodiment, the reaction can be initiated by a basic reagent having a $pk_a>10$. One non-limiting example of a useful basic reagent in this regard is sodium methoxide.

In another embodiment, the present subject matter relates to a method for the synthesis of a compound having Formula I or a stereoisomer thereof comprising a reaction between a fullerene and a compound having Formula II:

FORMULA I

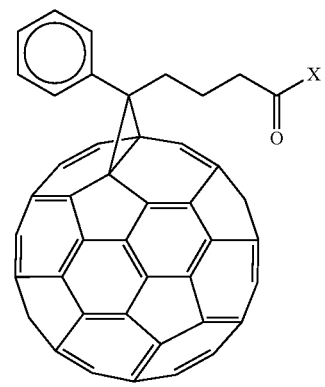

FORMULA II

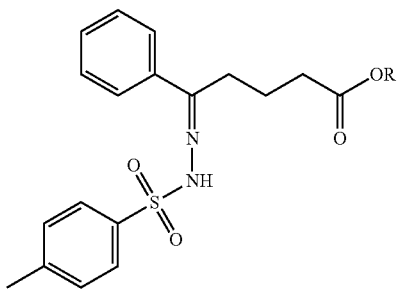

wherein X is $C_nH_{2n+1}$, R is $C_nH_{2n+1}$, and n=0 to 20; wherein the fullerene is selected from the group consisting of $C_{60}$, $C_{70}$, $C_{76}$, $C_{78}$, $C_{84}$, and $C_{90}$; wherein 0.25 mmol to 1.0 mmol of the compound having Formula II is used in the reaction; and wherein the reaction produces at least a 40% yield of the compound having Formula I.

In one embodiment in this regard, 0.5 mmol of the compound having Formula II is used in the reaction. In another embodiment, this reaction also produces no more than a 22% yield of a byproduct. The reaction can be initiated by a basic reagent having a $pk_a>10$. In a non-limiting embodiment, the basic reagent can be sodium methoxide.

In a further embodiment, the present subject matter relates to a method for the synthesis of a compound having Formula I or a stereoisomer thereof comprising a reaction between a fullerene and a compound having Formula II:

FORMULA I

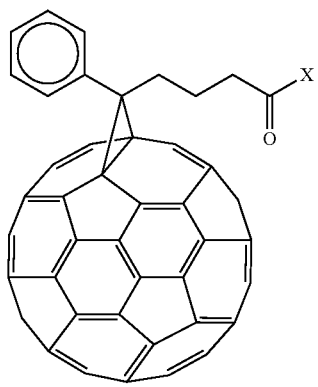

FORMULA II

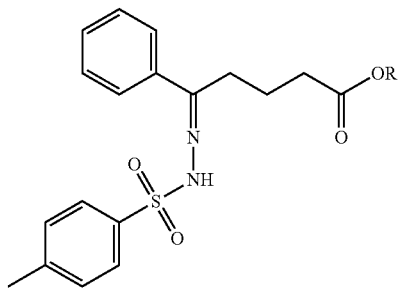

wherein X is $C_nH_{2n+1}$, R is $C_nH_{2n+1}$, and n=0 to 20; wherein the fullerene is selected from the group consisting of $C_{60}$, $C_{70}$, $C_{76}$, $C_{78}$, $C_{84}$, and $C_{90}$; wherein 0.25 mmol to 1.0 mmol of the compound having Formula II is used in the reaction; and wherein the reaction also produces no more than a 22% yield of a byproduct.

In one embodiment in this regard, 0.5 mmol of the compound having Formula II is used in the reaction. In another embodiment, this reaction produces at least a 40% yield of the compound having Formula I. The reaction can be initiated by a basic reagent having a $pk_a>10$. In a non-limiting embodiment, the basic reagent can be sodium methoxide.

In still another embodiment, the present subject matter relates to a method for the synthesis of a compound having Formula I or a stereoisomer thereof comprising a reaction between a fullerene and a compound having Formula II:

FORMULA I

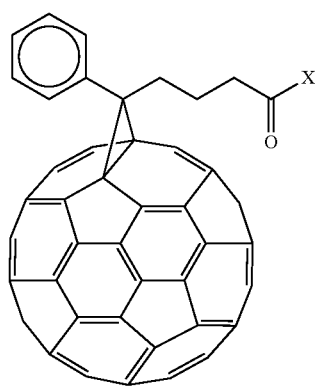

FORMULA II

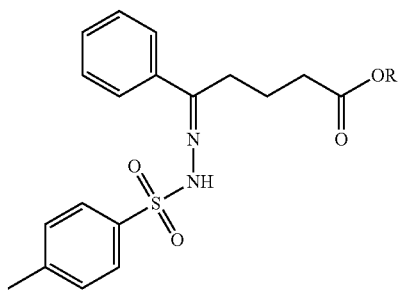

wherein X is $C_nH_{2n+1}$, R is $C_nH_{2n+1}$, and n=0 to 20; wherein the fullerene is selected from the group consisting of $C_{60}$, $C_{70}$, $C_{76}$, $C_{78}$, $C_{84}$, and $C_{90}$; wherein the fullerene and the compound having Formula II are present in the reaction at a molar ratio ranging from 1:2 to 2:1; and wherein the reaction also produces no more than a 22% yield of a byproduct.

In one embodiment in this regard, the fullerene and the compound having Formula II are present in the reaction at a molar ratio of 1:1. In another embodiment, the reaction produces at least a 40% yield of the compound having Formula I. The reaction can be initiated by a basic reagent having a $pk_a>10$. In a non-limiting embodiment, the basic reagent can be sodium methoxide.

Figure 11:
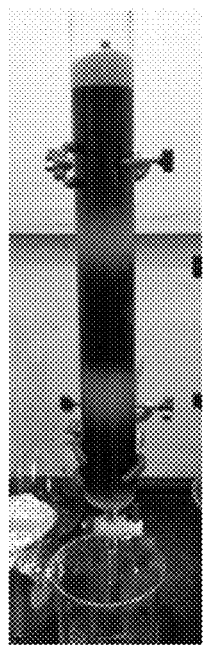
FIG. 11 is a picture illustrating the use of affinity chromatography to purify fullerenes and their derivatives.

In yet another embodiment, any of the above methods for the synthesis of a compound having Formula I or a stereoisomer thereof can further comprise a purification process, as shown in FIG. 11. The purification process can be one or more selected from the group consisting of affinity chromatography, reverse-phase chromatography, and adsorption chromatography.

Another embodiment of the present subject matter relates to a method for the synthesis of a compound having Formula I or a stereoisomer thereof comprising a first reaction and a second reaction:

Formula I

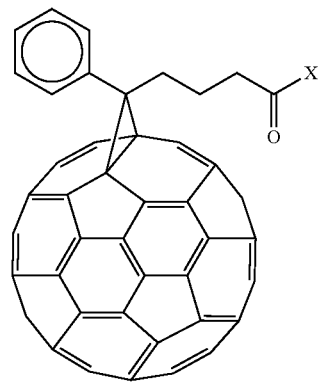

wherein X is $C_nH_{2n+1}$, and n=0 to 20; the first reaction comprising mixing a basic reagent with a compound having Formula II to produce a diazoalkane:

Formula II

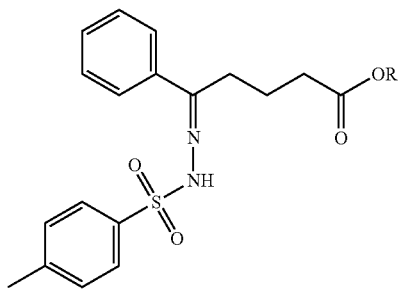

wherein R is $C_nH_{2n+1}$, and n=0 to 20; the second reaction comprising mixing the diazoalkane produced from the first reaction with a fullerene; wherein the fullerene is selected from the group consisting of $C_{60}$, $C_{70}$, $C_{76}$, $C_{78}$, $C_{84}$, and $C_{90}$; wherein the compound having Formula II and the basic reagent are present in the first reaction at a molar ratio ranging from 1:2 to 2:1; and wherein the first reaction and the second reaction produce at least a 40% yield of the compound having Formula I.

In one embodiment, the diazoalkane is 1-phenyl-1-(3-(methoxycarbonyl)propyl)diazomethane. The chemical structure of 1-phenyl-1-(3-(methoxycarbonyl)propyl)diazomethane is shown below.

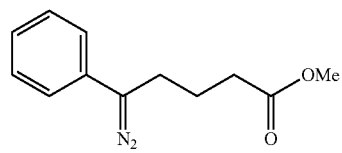

Accordingly, in one aspect, the first reaction produces 1-phenyl-1-(3-methoxycarbonyl)propyl)diazomethane using MBT as part of the starting material. In this aspect, a reaction scheme for the first reaction is as follows.

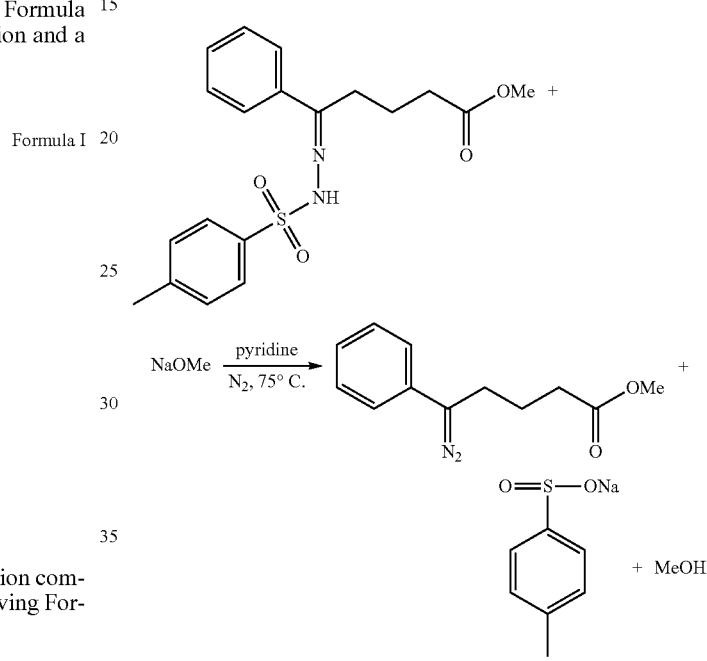

In another aspect, the second reaction produces [5,6] phenyl-butyric acid methyl ester by mixing 1-phenyl-1-(3-methoxycarbonyl)propyl)diazomethane, produced in the first reaction, with a fullerene, such as $C_{60}$. In this aspect, the reaction scheme of the second reaction is as follows.

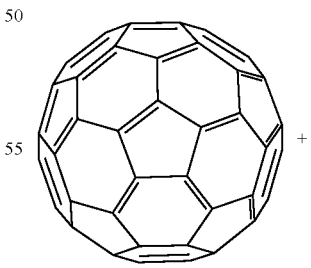

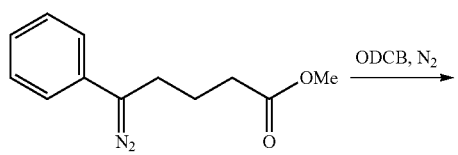

-continued

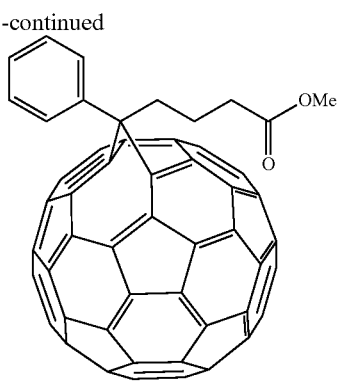

When the compound having Formula II and the basic reagent are present in the first reaction at a molar ratio ranging from 1:2 to 2:1, the first reaction and the second reaction produce at least a 40% yield of F1-OMe.

In another embodiment, PCBM is synthesized by heating F1-OMe within o-dichlorobenzene. The reaction scheme for this is shown as follows.

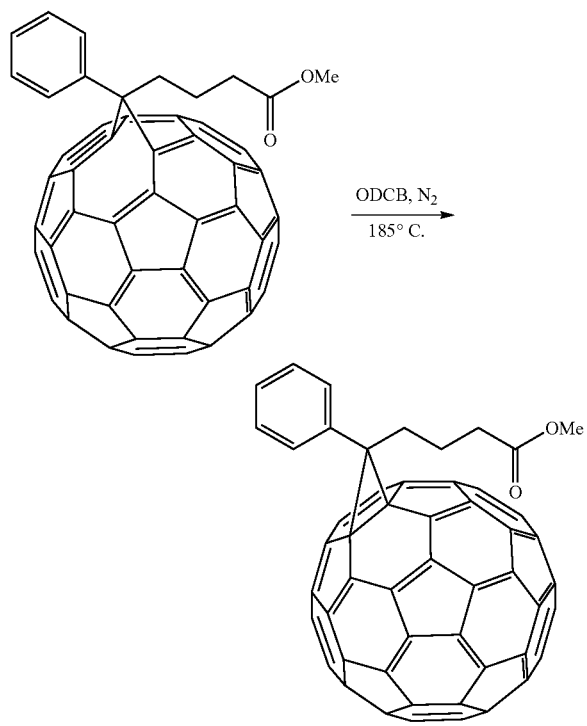

When the compound having Formula II and the basic reagent are present in the first reaction at a molar ratio ranging from 1:2 to 2:1, the first reaction and the second reaction produce a 40% yield of PCBM.

In another embodiment, the compound having Formula II and the basic reagent can be present in the first reaction at a molar ratio of 1:1.

In yet another aspect, the first and second reactions produce no more than a 22% yield of a byproduct.

In one embodiment, the basic reagent has a $pk_a > 10$. One non-limiting example of such a basic reagent is sodium methoxide.

Another embodiment of the present subject matter relates to a method for the synthesis of a compound having Formula I or a stereoisomer thereof comprising a first reaction and a second reaction:

Formula I

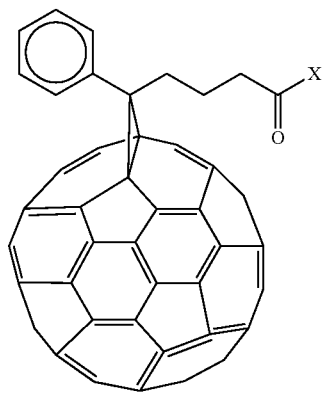

wherein X is $C_nH_{2n+1}$, and n=0 to 20; the first reaction comprising mixing a basic reagent with a compound having Formula II to produce a diazoalkane:

Formula II

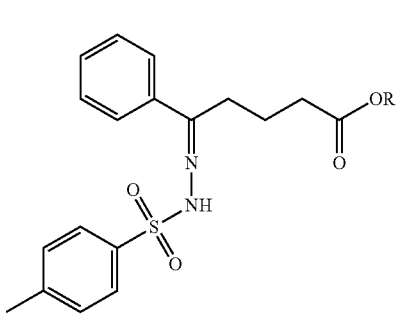

wherein R is $C_nH_{2n+1}$, and n=0 to 20; the second reaction comprising mixing the diazoalkane produced from the first reaction with a fullerene; wherein the fullerene is selected from the group consisting of $C_{60}$, $C_{70}$, $C_{76}$, $C_{78}$, $C_{84}$, and $C_{90}$; wherein the compound having Formula II and the basic reagent are present in the first reaction at a molar ratio ranging from 1:3 to 4:3; and wherein the first reaction and the second reaction produce at least a 40% yield of the compound having Formula I.

In one embodiment in this regard, the compound having Formula II and the basic reagent are present in the first reaction at a molar ratio of 1:1. In another embodiment, the first and second reactions produce no more than a 22% yield of a byproduct. The basic reagent used can have a $pk_a > 10$. In a non-limiting embodiment, the basic reagent can be sodium methoxide.

A further embodiment of the present subject matter relates to a method for the synthesis of a compound having Formula I or a stereoisomer thereof comprising a first reaction and a second reaction:

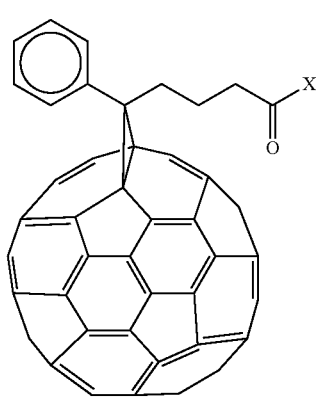

Formula I wherein X is $C_nH_{2n+1}$, and n=0 to 20; the first reaction comprising mixing a basic reagent with a compound having Formula II to produce a diazoalkane:

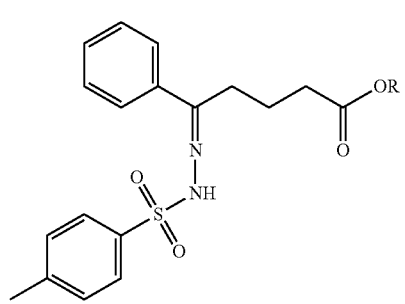

Formula II wherein R is $C_nH_{2n+1}$, and n=0 to 20; the second reaction comprising mixing the diazoalkane produced from the first reaction with a fullerene; wherein the fullerene is selected from the group consisting of $C_{60}$, $C_{70}$, $C_{76}$, $C_{78}$, $C_{84}$, and $C_{90}$; wherein the compound having Formula II and the basic reagent are present in the first reaction at a molar ratio ranging from 1:3 to 4:3; and wherein the first reaction and the second reaction also produce no more than a 22% yield of a byproduct.

In one embodiment in this regard, the compound having Formula II and the basic reagent are present in the first reaction at a molar ratio of 1:1. In another embodiment, the first and second reactions produce at least a 40% yield of the compound having Formula I. The basic reagent used can have a $pk_a>10$. In a non-limiting embodiment, the basic reagent can be sodium methoxide.

A still further embodiment of the present subject matter relates to a method for the synthesis of a compound having Formula I or a stereoisomer thereof comprising a first reaction and a second reaction:

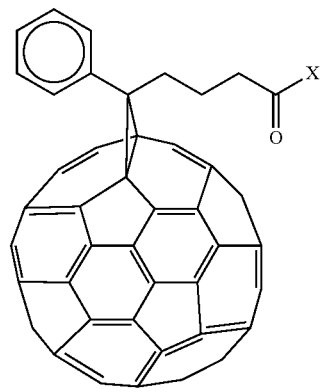

Formula I wherein X is $C_nH_{2n+1}$, and n=0 to 20; the first reaction comprising mixing a basic reagent with a compound having Formula II to produce a diazoalkane:

Formula II wherein R is $C_nH_{2n+1}$, and n=0 to 20; the second reaction comprising mixing the diazoalkane produced from the first reaction with a fullerene; wherein the fullerene is selected from the group consisting of $C_{60}$, $C_{70}$, $C_{76}$, $C_{78}$, $C_{84}$, and $C_{90}$; wherein 0.25 mmol to 1.0 mmol of the compound having Formula II is used in the first reaction; and wherein the first reaction and the second reaction produce at least a 40% yield of the compound having Formula I.

In one embodiment in this regard, 0.5 mmol of the compound having Formula II is used in the first reaction. In another embodiment, the first and second reactions produce no more than a 22% yield of a byproduct. The basic reagent used can have a $pk_a>10$. In a non-limiting embodiment, the basic reagent can be sodium methoxide.

Yet another embodiment of the present subject matter relates to a method for the synthesis of a compound having Formula I or a stereoisomer thereof comprising a first reaction and a second reaction:

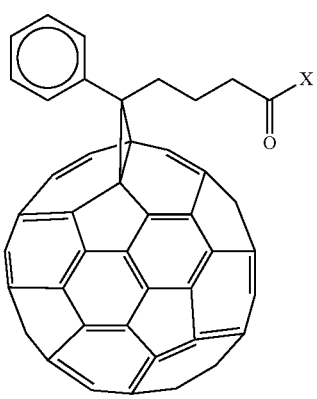

Formula I wherein X is $C_nH_{2n+1}$, and n=0 to 20; the first reaction comprising mixing a basic reagent with a compound having Formula II to produce a diazoalkane:

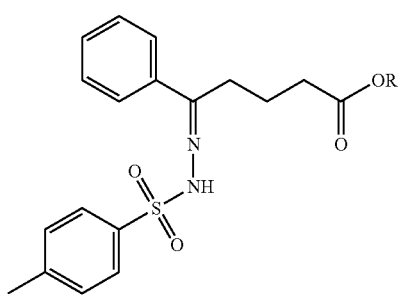

Formula II wherein R is $C_nH_{2n+1}$, and n=0 to 20; the second reaction comprising mixing the diazoalkane produced from the first reaction with a fullerene; wherein the fullerene is selected from the group consisting of $C_{60}$, $C_{70}$, $C_{76}$, $C_{78}$, $C_{84}$, and $C_{90}$; wherein 0.25 mmol to 1.0 mmol of the compound having Formula II is used in the first reaction; and wherein the first reaction and the second reaction also produce no more than a 22% yield of a byproduct.

In one embodiment in this regard, 0.5 mmol of the compound having Formula II is used in the first reaction. In another embodiment, the first and second reactions produce at least a 40% yield of the compound having Formula I. The basic reagent used can have a $pk_a > 10$. In a non-limiting embodiment, the basic reagent can be sodium methoxide.

In yet another embodiment, any of the above methods for the synthesis of a compound having Formula I or a stereoisomer thereof can further comprise a purification process, as shown in FIG. 11. The purification process can be one or more selected from the group consisting of affinity chromatography, reverse-phase chromatography, and adsorption chromatography.

A further embodiment of the present subject matter relates to a method for the synthesis of a compound having Formula I or a stereoisomer thereof comprising a reaction between a diazoalkane and a fullerene:

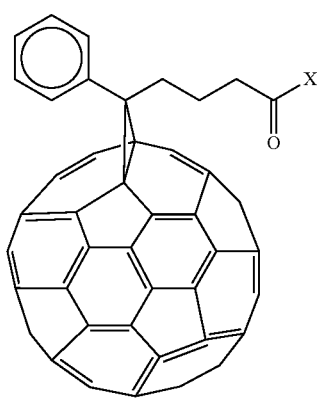

Formula I wherein X is $C_nH_{2n+1}$, and n=0 to 20; wherein the fullerene is selected from the group consisting of $C_{60}$, $C_{70}$, $C_{76}$, $C_{78}$, $C_{84}$, and $C_{90}$; and wherein the reaction produces at least a 40% yield of the compound having Formula I.

In one embodiment in this regard, the reaction also produces no more than a 22% yield of a byproduct.

Another embodiment of the present subject matter relates to a method for the synthesis of a compound having Formula I or a stereoisomer thereof comprising a reaction between a diazoalkane and a fullerene:

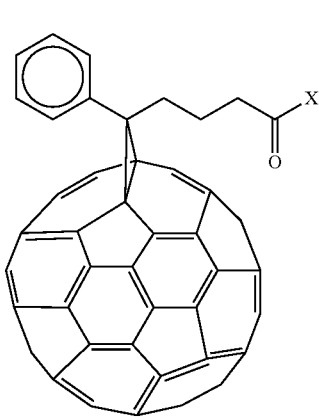

Formula I wherein X is $C_nH_{2n+1}$, and n=0 to 20; wherein the fullerene is selected from the group consisting of $C_{60}$, $C_{70}$, $C_{76}$, $C_{78}$, $C_{84}$, and $C_{90}$; and wherein the reaction also produces no more than a 22% yield of a byproduct.

In one embodiment in this regard, the reaction produces at least a 40% yield of the compound having Formula I.

In yet another embodiment, any of the above methods for the synthesis of a compound having Formula I or a stereoisomer thereof can further comprise a purification process, as shown in FIG. 11. The purification process can be one or more selected from the group consisting of affinity chromatography, reverse-phase chromatography, and adsorption chromatography.

EXAMPLES

The examples below demonstrate various embodiments of the present subject matter.

Example 1

Synthesis of F1-OMe

Figure 7:
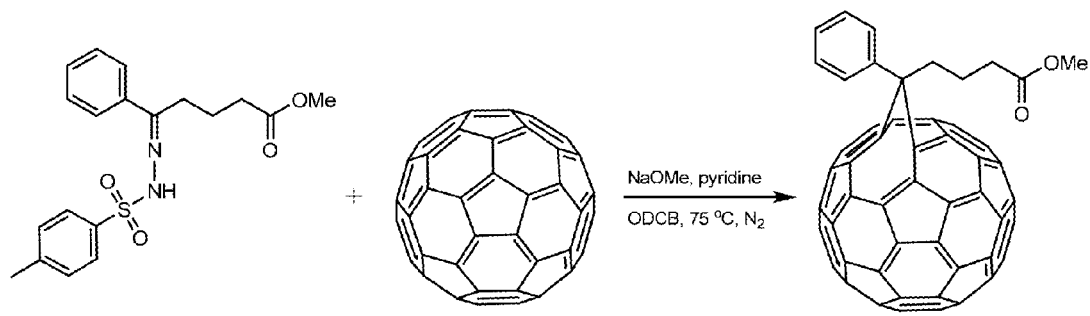
FIG. 7 shows the reaction scheme for the synthesis of the compound having Formula I.

Methyl 4-benzoylbutyrate p-tosylhydrazone (MBT, 0.5 mmol) and sodium methoxide (NaOMe, 0.5 mmol) were added into a 100 mL dried two-necked flask and vacuumed for three times (15 min per time). 10 mL pyridine was then injected to the flask provided with $N_2$ inlet and stirred for 15 min. 0.5 mmol $C_{60}$ was dissolved in 20 mL o-dichlorobenzene (ODCB) in a 100 mL bottom flask. The $C_{60}$ solution was degassed (bubbling by $N_2$) for 15 min and then injected to the pyridine solution. The mixture was stirred at 75° C. for 22 h with $N_2$ inlet. The total reaction scheme is shown in FIG. 7.

Example 2

Two-Step Synthesis of F1-OMe

Figure 8:
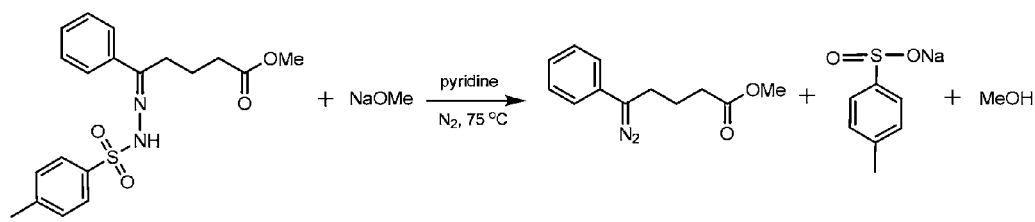
FIG. 8 shows the reaction scheme of the first reaction for the synthesis of a diazoalkane.

Two reactions were involved herein. The first reaction was the generation of diazo compounds from tosylhydrazones. The pyridine was used as solvent. In order to efficiently generate diazo compounds, a temperature of about 70° C. is required. The reaction scheme of the first reaction is shown in FIG. 8.

Figure 9:
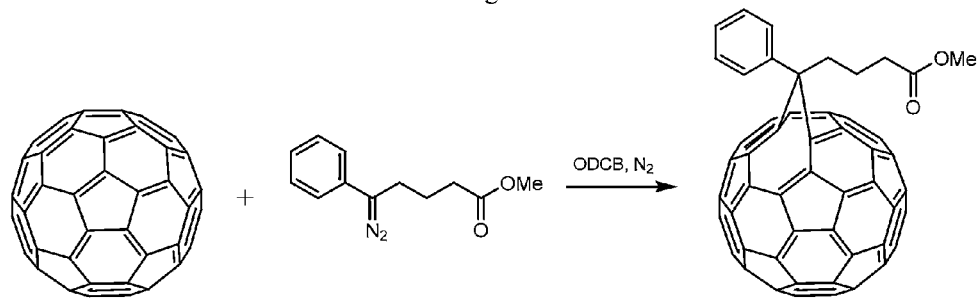
FIG. 9 shows the reaction scheme of the second reaction for the synthesis of F1-OMe.

The second reaction was the generation of F1-OMe by a typical diazo addition route. The ODCB was used as solvent. Once the diazo compounds were formed, they were rapidly trapped by $C_{60}$. The second reaction scheme is shown in FIG. 9.

The conversion (X), yield of F1-OMe (Y) and yield of byproduct (Z) were defined as below:

$$X = \frac{\text{moles of } C60 \text{ converted}}{\text{moles of } C60 \text{ initially}}$$

$$Y = \frac{\text{moles of } F1-OMe}{\text{moles of } C60 \text{ initially}}$$

$$Z = X - Y$$

After the reaction, the solution was transferred to a round bottom flask and concentrated in vacuum and purified by column chromatography. The first fraction (purple) containing unreacted $C_{60}$ was collected, concentrated in vacuum to about 20 mL and precipitated with diethyl ether (120 mL). The suspension was sonicated for 1 min and centrifuged. The residue was treated with diethyl ether twice in the same manner and dried in vacuum at 70° C. overnight. The dry unreacted $C_{60}$ was obtained and can be reused. Yield: 136.6 mg (37.95%). The second fraction (brown) containing F1-OMe was collected and purified in the same manner for $C_{60}$, using methanol instead of diethyl ether as precipitator. Yield: 185.8 mg (40.83%).

Example 3

Figure 10:
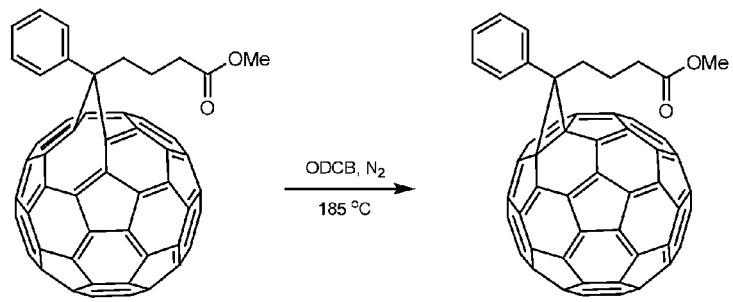
FIG. 10 shows the reaction scheme for the synthesis of PCBM from F1-OMe.

Synthesis of PCBM 185.8 mg F1-OMe were added into a 100 mL dried two-necked flask and vacuumed for three times. 30 mL ODCB was added with stirring and heated to reflux for 20 h. The isomerization was monitored by HPLC. The resulting brown solution was concentrated in vacuo to about 15 mL and precipitated with methanol as described for the F1-OMe. The final product was analyzed by HPLC and the purity was calculated to 99.93%. The reaction scheme is shown in FIG. 10.

Example 4

Synthesis of PCBM Using Various Reaction Conditions

As shown in Table 1, PCBM was synthesized using various amounts of MBT, NaOMe, and $C_{60}$.

TABLE 1

Synthesis of PCBM using various reaction conditions

| Num. | $C_{60}$ (mmol) | Methyl 4-Benzoylbutyrate p-Tosylhydrazone (MBT) (mmol) | NaOMe (mmol) | $C_{60}$ (unconverted) % | $C_{60}$ (conversion) % X | F1—OMe (yield) % Y | Byproduct (yield) % Z | Y:X |
|---|---|---|---|---|---|---|---|---|
| 1 | 0.5 | 0.5 | 1.5 | 100 | 0 | 0 | 0 | — |
| 2 | 0.5 | 0.5 | 1.0 | 25.44 | 74.56 | 36.22 | 38.33 | 0.49 |
| 3 | 0.5 | 0.5 | 0.75 | 19.53 | 80.47 | 42.94 | 37.53 | 0.53 |
| 4 | 0.5 | 0.5 | 0.625 | 23.86 | 76.14 | 42.97 | 33.17 | 0.56 |
| 5 | 0.5 | 0.5 | 0.5 | 37.95 | 62.05 | 40.83 | 21.22 | 0.66 |
| 6 | 0.5 | 0.5 | 0.375 | 42.33 | 57.67 | 33.12 | 24.55 | 0.57 |
| 7 | 0.5 | 0.75 | 0.75 | 14.53 | 85.47 | 43.25 | 42.22 | 0.51 |
| 8 | 0.5 | 1 | 1 | 3.94 | 96.09 | 32.86 | 63.20 | 0.34 |
| 9 | 0.5 | 0.25 | 0.25 | 61.14 | 38.86 | 22.66 | 16.20 | 0.58 |

As highlighted in Table 1, the row 5 contains the preferable conditions for synthesizing PCBM in a yield of at least 40%.

With the information contained herein, various departures from precise description of the present subject matter will be readily apparent to those skilled in the art to which the present subject matter pertains, without departing from the spirit and the scope of the below claims. The present subject matter is not to be considered limited in scope to the procedures, properties or components defined, since the preferred embodiments and other descriptions are intended only to be illustrative of particular aspects of the presently provided subject matter. Indeed, various modifications of the described modes for carrying out the present subject matter which are obvious to those skilled in biomechanical or related fields are intended to be within the scope of the following claims.

We claim:

1. A method for the synthesis of a compound having Formula I or a stereoisomer thereof comprising a reaction between a fullerene and a compound having Formula II:

FORMULA I

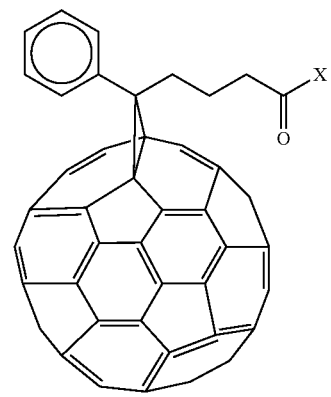

FORMULA II

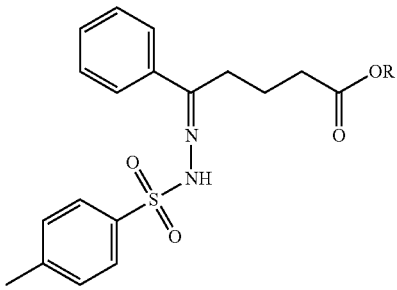

wherein
X is $C_nH_{2n+1}$,
R is $C_nH_{2n+1}$, and
n=0 to 20;
wherein the fullerene is selected from the group consisting of $C_{60}$, $C_{70}$, $C_{76}$, $C_{78}$, $C_{84}$, and $C_{90}$;
wherein the fullerene and the compound having Formula II are present in the reaction at a molar ratio of about 1:1; and
wherein the reaction produces at least a 40% yield of the compound having Formula I.

2. The method of claim 1, wherein the reaction also produces no more than a 22% yield of a byproduct.

3. The method of claim 1, wherein the reaction is initiated by a basic reagent having a $pk_a$>10.

4. The method of claim 3, wherein the basic reagent is sodium methoxide.

5. The method of claim 1 further comprising a purification process.

6. The method of claim 5, wherein the purification process is one or more selected from the group consisting of affinity chromatography, reverse-phase chromatography, and adsorption chromatography.

7. A method for the synthesis of a compound having Formula I or a stereoisomer thereof comprising a first reaction and a second reaction:

FORMULA I

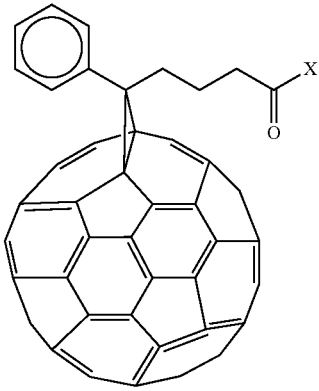

wherein
X is $C_nH_{2n+1}$, and
n=0 to 20;
the first reaction comprising mixing a basic reagent with a compound having Formula II to produce a diazoalkane:

FORMULA II

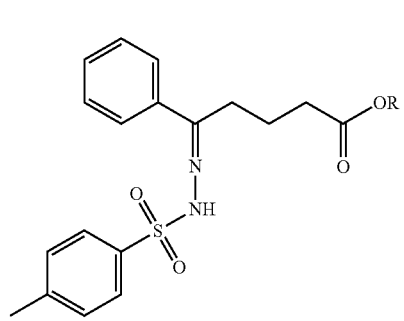

wherein
R is $C_nH_{2n+1}$, and
n=0 to 20;
the second reaction comprising mixing the diazoalkane produced from the first reaction with a fullerene;
wherein the fullerene is selected from the group consisting of $C_{60}$, $C_{70}$, $C_{76}$, $C_{78}$, $C_{84}$, and $C_{90}$;
wherein the compound having Formula II and the basic reagent are present in the first reaction at a molar ratio of about 1:1; and
wherein the first reaction and the second reaction produce at least a 40% yield of the compound having Formula I.

8. The method of claim 7, wherein the fullerene and the compound having Formula II are present in the second reaction at a molar ratio of about 1:1.

9. The method of claim 7, wherein the first and second reaction produce no more than a 22% yield of a byproduct.

10. The method of claim 7, wherein the basic reagent has a $pk_a$>10.

11. The method of claim 7, wherein the basic reagent is sodium methoxide.

12. The method of claim 7 further comprising a purification process.

13. The method of claim 12, wherein the purification process is one or more selected from the group consisting of affinity chromatography, reverse-phase chromatography, and adsorption chromatography.

* * * * *